United States Patent
Vince et al.

(10) Patent No.: US 6,200,268 B1
(45) Date of Patent: Mar. 13, 2001

(54) VASCULAR PLAQUE CHARACTERIZATION

(75) Inventors: D. Geoffrey Vince, University Heights; Barry D. Kuban, Avon Lake; Anuja Nair, Cleveland Heights, all of OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/394,140

(22) Filed: Sep. 10, 1999

(51) Int. Cl.$^7$ ................................. A61B 8/00; A61B 8/12
(52) U.S. Cl. ......................... 600/443; 600/463; 600/467
(58) Field of Search .................................. 600/437, 443, 600/447, 463, 455–456, 466–467, 471, 407; 128/916

(56) References Cited

U.S. PATENT DOCUMENTS

| | | | |
|---|---|---|---|
| 5,582,171 | * 12/1996 | Chornenky et al. | 600/407 |
| 5,885,218 | * 3/1999 | Teo et al. | 600/443 |
| 6,019,726 | * 2/2000 | Webb | 600/459 |
| 6,095,976 | * 8/2000 | Nachtomy et al. | 600/443 |
| 6,102,862 | * 8/2000 | Grunwald et al. | 600/447 |
| 6,120,445 | * 9/2000 | Grunwald | 600/437 |

FOREIGN PATENT DOCUMENTS

PCT/GB97/03259  6/1998  (WO).

OTHER PUBLICATIONS

Imaging Systems and Technology—John Wiley & Sons, Inc. vol. pp. 5, 52–60 (1997).

Histopathologic Validation of Intracoronary Ultrasound Imaging—Peters, et al. pp. 230–pp. 241 (Date May–Jun. 1994) Journal of the American Society of Echocardiography.

High Resolution Ultrasonic Backscatter Coefficient Estimation Based on Autoregressive Spectral Estimation Using Burg's Algorithm—Wear, Wagner and Garra (IEEE Transactions and Medical Imaging, vol. 3, No. Sep. 1994) (p. 500 to p. 507).

Characterisation of coronary atherosclerotic morphology by spectral analysis of radiofrequency signal: in vitro intravascular ultrasound study with histological and radiological validation. Heart, (1998), p. 459–467.

Characterisation of Atherosclerotic Plaque By Spectral Analysis of Intravascular Ultrasound: An In Vitro Methodology. Ultrasound in Med. & Biol., vol. 23, No. 2 pp. 191–203, 1997.

* cited by examiner

*Primary Examiner*—Marvin M. Lateef
*Assistant Examiner*—Ali M. Imam
(74) *Attorney, Agent, or Firm*—Calfee, Halter & Griswold LLP

(57) ABSTRACT

A method and system for characterizing plaque components within a vascular object is provided. The vascular object is scanned with an ultrasonic device and backscatter signal data is collected. Histology images are prepared and digitized which correspond to the scanned vascular sections. A plaque component is selected on the histology image and its coordinates are mapped to a corresponding location on an IVUS image constructed from the backscatter signal. The IVUS image location is then translated to the corresponding signal section of the raw backscatter signal. Frequency analysis is performed on the signal section to determine its signal properties. The signal properties are correlated to the selected plaque component of the histology image and stored in a plaque characterization database. The process is then repeated for all plaque components and other tissue types found within the vascular object and stored in the database. With the present invention, the components of the vascular object such as a blood vessel can be identified directly from the raw backscatter signal by matching its signal properties with the signal properties of the database, thus, identifying plaque components or other tissue components in vivo and in real-time.

19 Claims, 5 Drawing Sheets

VASCULAR PLAQUE CHARACTERIZATION

BACKGROUND OF THE INVENTION

The present invention relates to the intravascular ultrasound analysis arts. It finds particular application to a method and system for quantitative component identification within a vascular object including characterization of plaque. It will be appreciated that the present invention will also find application to other types objects which can be scanned with an ultrasonic device.

Ultrasonic imaging of portions of a patient's body provides a useful tool in various areas of medical practice for determining the best type and course of treatment. Imaging of the coronary vessels of a patient by ultrasonic techniques can provide physicians with valuable information. For example, the image data may show the extent of a stenosis in a patient, reveal progression of disease, help determine whether procedures such as angioplasty or atherectomy are indicated or whether more invasive procedures may be warranted.

In a typical ultrasound imaging system, an ultrasonic transducer is attached to the end of a catheter that is carefully maneuvered through a patient's body to a point of interest such as within a blood vessel. The transducer is a single-element crystal or probe which is mechanically scanned or rotated back and forth to cover a sector over a selected angular range. Acoustic signals are transmitted during the scanning and echoes from these acoustic signals are received to provide data representative of the density of tissue over the sector. As the probe is swept through the sector, many acoustic lines are processed building up a sector-shaped image of the patient. After the data is collected, images of the blood vessel are reconstructed using well-known techniques and the images are visually analyzed by a cardiologist to assess the vessel components and plaque content.

Typically, the ultrasonic image data is transferred to a VHS videotape, digitized and then analyzed. This process, however, loses image resolution since the videotape has a lower resolution than the originally collected ultrasound data. Losing image resolution may result in an inaccurate evaluation of a vessel and its plaque content. Furthermore, certain image characteristics like brightness and contrast will be different for different patients or could vary for the same patient if the cardiologist varies the settings on the IVUS console. The images that are recorded on the videotapes are the same images viewed on the IVUS console screen and, thus, subject to the settings on the console. Since plaque is identified by its appearance on the screen, errors may occur in the analysis if the screen settings have been modified.

The present invention provides a new and unique intravascular ultrasonic analysis method and system with cures the above problems and others.

SUMMARY OF THE INVENTION

In accordance with the present invention, a new and unique method of identifying components within a vascular object from an ultrasonic signal is provided. An ultrasonic signal is transmitted within a selected region of the vascular object and a backscatter signal reflected from the vascular object is collected. An IVUS image of the selected region is reconstructed from the backscatter signal. A histology image of the selected region of the vascular object is prepared which distinguishes different components of the vascular object. A region of interest is selected from the histology image which represents one component from the different components of the vascular object. The region of interest is at a coordinate location on the histology image. The coordinate location is mapped to a location on the IVUS image which corresponds to the coordinate location. The location on the IVUS image is then translated to a signal portion in the backscatter signal which corresponds to the IVUS location. The signal portion represents a signal signature of the one component of the vascular object which is then correlated to the one component.

In accordance with a more limited aspect of the present invention, the method further includes performing a signal analysis on the signal portion to determine signal properties of the signal portion where the signal signature includes the signal properties.

In accordance with another aspect of the present invention, a method of identifying components of a vascular object from an ultrasonic signal is provided. An ultrasonic signal is transmitted within the vascular object where the vascular object reflects portions and absorbs portions of the ultrasonic signal. The reflected portions are collected as a backscatter signal which includes signal properties. A database is provided which associates vascular components to signal properties. The signal properties of the backscatter signal are compared to the signal properties in the database to determine a match. A vascular component is then assigned to the signal properties of the backscatter signal if a match is determined, thus, identifying the signal.

In accordance with a more limited aspect of the present invention, an intravascular ultrasound image is generated from the backscatter signal which distinguishes different vascular components based on the vascular component assigned to the signal properties of the backscatter signal.

In accordance with a more limited aspect of the present invention, the database is pregenerated by correlating vascular components from a histology image to corresponding signal properties from a backscatter signal.

In accordance with a more limited aspect of the present invention, a relationship is determined between two vascular components within the backscatter signal based on a location of the components along the backscatter signal.

In accordance with another aspect of the present invention, a method for characterizing a plaque component within a vascular object based on an ultrasonic backscatter signal collected from a selected section of the vascular object is provided. A histology image of the selected section is prepared. An area in the histology image is selected which represents a plaque component. The area in the histology image is then corresponded to a segment of the backscatter signal where the segment includes signal properties. The plaque component is then associated to the signal properties of the segment.

One advantage of the present invention is that it can automatically identify plaque components from a raw backscatter signal.

Another advantage of the present invention is that a blood vessel can be analyzed in real-time to identify plaque content while a patient is on the operating table. The present invention provides a database which identifies signal properties for each type of plaque component, thus, eliminating the need to perform image analysis by an operator.

Another advantage of the present invention is that it accurately identifies segments of a backscatter signal scan line based on previously generated histology information.

Yet another advantage of the present invention is that the distance of a plaque component from the vessel wall can be determined directly from a backscatter signal. Therefore, it can be determined whether a plaque component is stable or unstable.

Still further advantages of the present invention will become apparent to those of ordinary skill in the art upon reading and understanding the following detailed description of the preferred embodiments.

BRIEF DESCRIPTION OF THE DRAWINGS

The following is a brief description of each drawing used to describe the present invention, and thus, are being presented for illustrative purposes only and should not be imitative of the scope of the present invention, wherein.

DETAILED DESCRIPTION OF THE PREFERRED EMBODIMENTS

Figure 1:
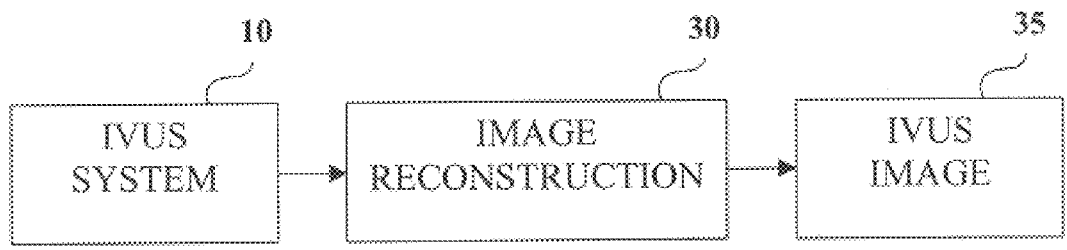
FIG. 1 is a block diagram of an overall ultrasonic imaging system.

With reference to FIG. 1, an overall intravascular ultrasound (IVUS) system is shown. An IVUS system console 10 collects ultrasonic data from a transducer. The transducer is attached to the end of a catheter that is carefully maneuvered through a patient's body to a point of interest. In the present system, the catheter is maneuvered through the interior of a vascular organ in order to obtain intravascular ultrasound data of the surrounding vascular tissue. The IVUS system console 10 is, for example, a C-VIS Clearview Imaging System and the transducer is a single element mechanically rotated ultrasonic device having at least a frequency of 20 MHz. The ultrasonic device may also be an array of transducers circumferentially positioned to cover 360° where each transducer radially acquires radio frequency data from a fixed position.

Figure 2:
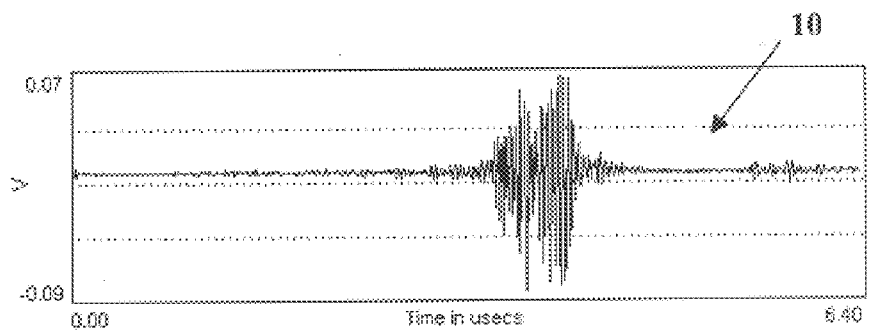
FIG. 2 illustrates an exemplary backscatter scan line.
Figure 3:
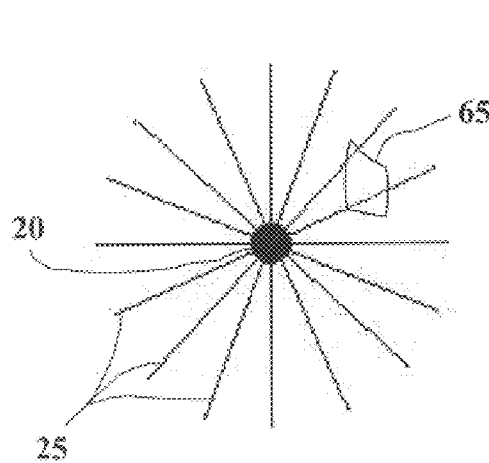
FIG. 3 illustrates a transducer and a plurality of scan lines.
Figure 4:
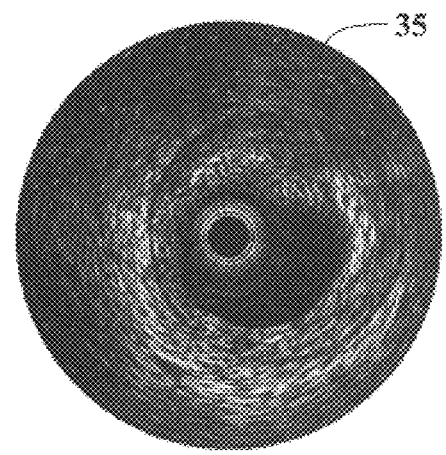
FIG. 4 is an exemplary intravascular ultrasound image.

An exemplary process for collecting ultrasound data is as follows. A transducer is inserted into a vascular object until it reaches a selected section of the vascular object to be analyzed. The transducer is pulsed and then acquires echoes of a backscatter signal reflected from the tissue of the vascular object. Different types and densities of tissue absorb and reflect the ultrasound pulse differently. The backscatter signal defines one scan line. An exemplary backscatter signal 15 is shown in FIG. 2 with frequency along the y-axis. The transducer is rotated 1.5 degrees and pulsed again. This is repeated for 240 scan lines around 360 degrees. Of course, any number of scan lines can be used. FIG. 3 shows a representation of the transducer 20 and a plurality of scan lines 25. The number of samples acquired in each scan line controls the depth of the echoes recorded by the transducer and ultimately the resolution of the image. An image reconstruction processor 30 reconstructs an IVUS image 35 from the acquired raw radio frequency ultrasound data. The reconstruction is performed using any image reconstruction routine as known in the art. An exemplary image reconstruction processor is a computer executing image reconstruction software. An exemplary reconstructed IVUS image 35 is shown in FIG. 4 which shows a cross-sectional view of a blood vessel.

Figure 5:
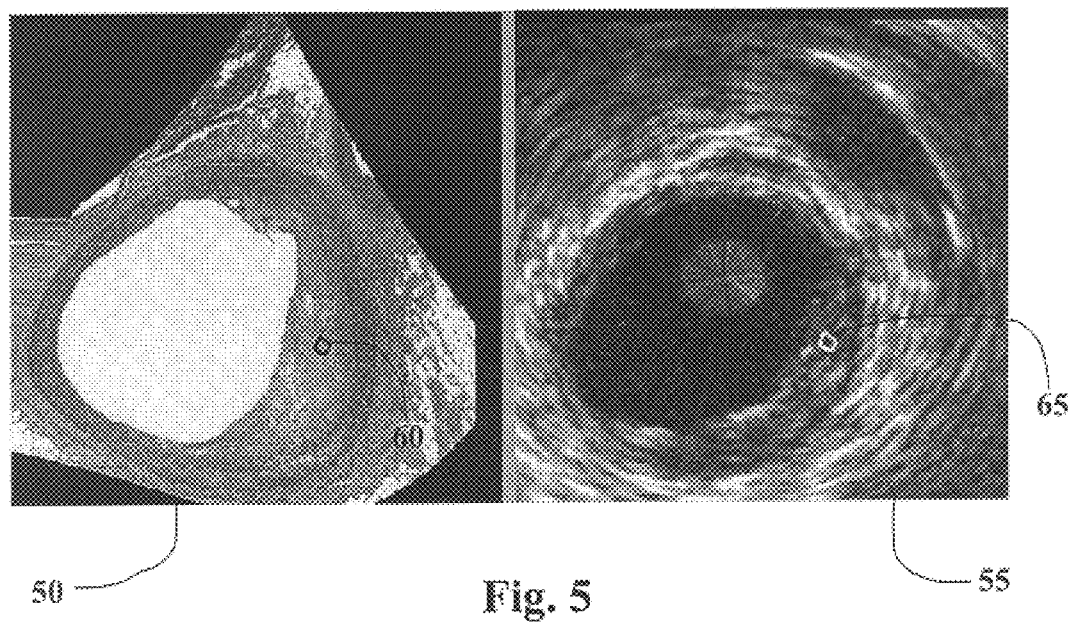
FIG. 5 shows a correspondence between a histology image and an IVUS image in accordance with the present invention.

Once the ultrasound backscatter signals are collected, a histology correlation is prepared. The imaged sections of the blood vessel are cross-sectioned for histology. The sections were previously marked, for example with a suture, so that the histology can be corresponded to the IVUS images of the sections. A histology image 50 is prepared and digitized as shown in FIG. 5 and its corresponding IVUS image 55 is shown next to it. The histology image 50 is prepared with a fixing and staining process which is well known in the art. The staining is very precise for identifying a type of tissue or chemical in the vessel. The histology image shows different tissue types with different colors which are identifiable by a trained operator. The types of plaque components which may be found in a blood vessel include collagen, calcium, necrotic areas, lipids and cholesterol. Other vessel components that can be identified in the histology image are the lumen, the vessel wall, the medial-adventitial boundary, and thrombus areas. To accurately match the coordinates of the images, the histology image 50 is warped to fit the contour of the IVUS image 55. The warping removes histological preparation artifacts caused by cutting the tissue.

From the digitized histology image 50, an operator selects a region of interest 60 which encloses a selected plaque component. The x,y coordinates defining the region of interest 60 are determined from the histology image. The coordinates are then mapped to the same location in the corresponding IVUS image 55 and an IVUS region of interest 65 that corresponds to the histology region of interest 60 is determined. IVUS coordinates that define the IVUS region of interest 65 are determined and are then translated back to the raw backscatter signal to determine the scan lines and portions of the scan lines which generated the region of interest 65.

Figure 6A:
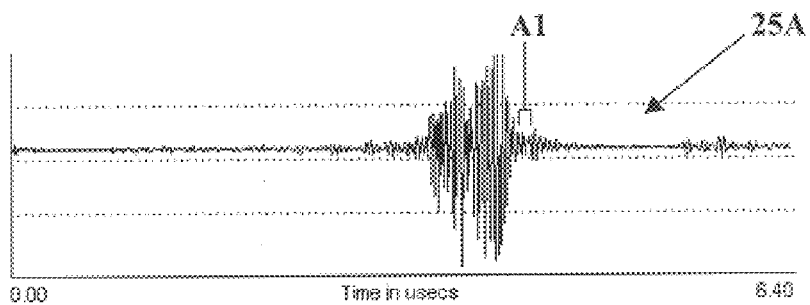
FIGS. 6A and 6B each show a scan line associated with the region of interest of FIG. 5.
Figure 6B:
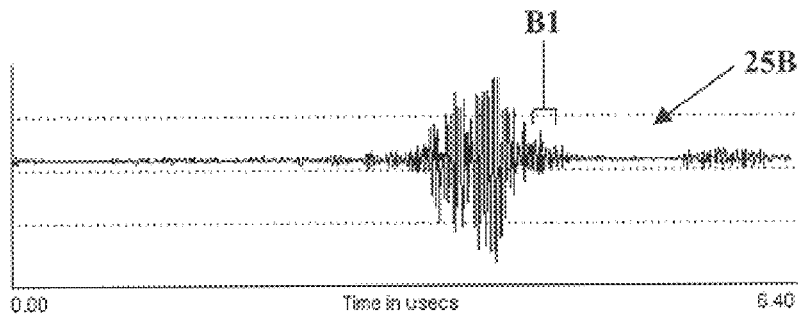

With reference again to FIG. 3, the region of interest 65 may overlap more than one scan line 25, in this case, scan lines 25A and 25B. From the IVUS coordinates, the portions of each scan line attributing to the region of interest 65 are determined. Signal analysis is then performed on each selected portion of the scan lines. FIGS. 6a and 6b show exemplary backscatter signals for scan lines 25A and 25B. All tissues that receive the pulsed signal reflect and transmit some of the pulse energy that is received by the transducer as the backscatter or reflected signal. The difference between the transmitted and received signals is that the frequency of the transmitted signal is constant, for example 30 MHz, and the backscatter signal is made up of signals at different frequencies. Each frequency is characteristic of the tissue that reflected it. Therefore, performing a frequency analysis on the backscatter signal provides for the detection of different frequencies in the radio frequency data. In other words, the frequency information obtained from the backscattered signal serves as a signature for each plaque component and other vessel components that are present.

Figure 7:
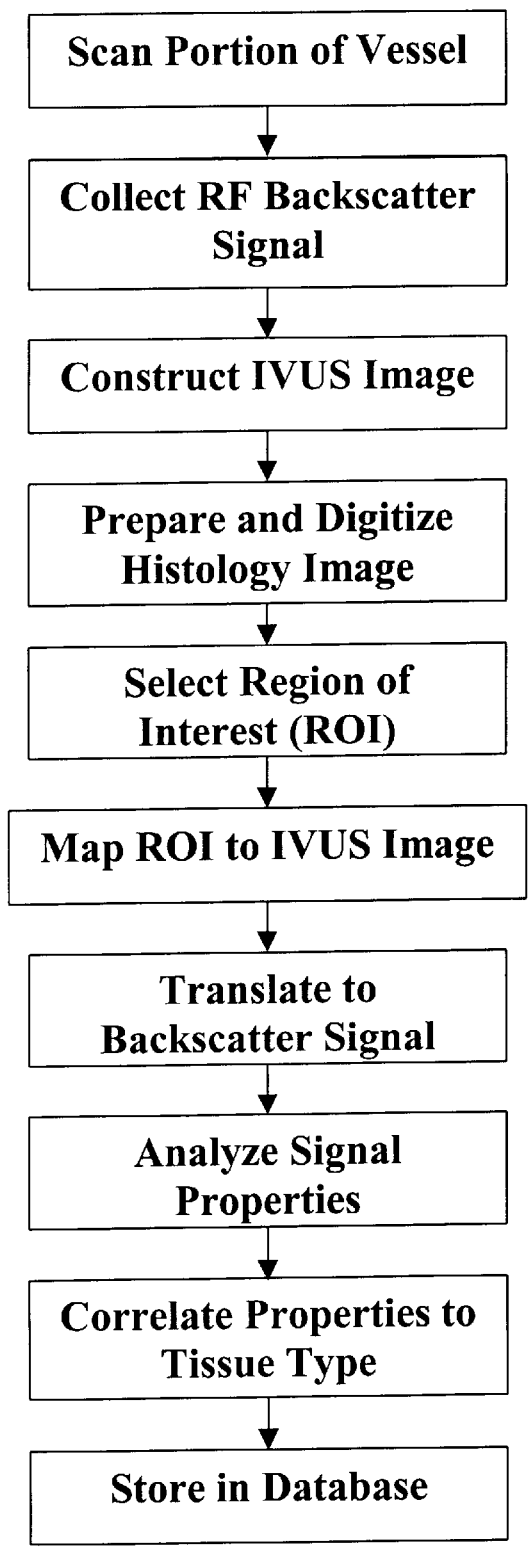
FIG. 7 illustrates a process for generating a signal signature characterization database in accordance with the present invention.

With further reference to FIGS. 6A and 6B, to accurately identify the signal signature of the tissue component within the region of interest 65, a particular segment of each backscatter signal 25A and 25B that corresponds to the region of interest 65, in this case, sections A1 and B1, is determined. In the preferred embodiment, a fast Fourier transform performs frequency analysis on the signal segments A1 and B1. The analysis provides signal properties characteristic of the plaque content within the region of interest 65 and serves as a signal signature for the plaque content. In the present example, since two signal segments A1 and B1 comprise the region of interest 65, the final signal properties are determined by averaging the signal properties from each segment. Additional analysis can be performed such as spectral density and/or power spectrum analysis to provide more information regarding the signal properties such as amount of energy and the density of a signal that is present at a specific frequency. Attenuation may also be a parameter. With this information, the amount of calcium or lipid present in a certain part of the plaque can be determined. The final signal parameters corresponding to the plaque component within the region of interest 65, which represents the plaque content from the histology region of interest 55, are stored in a look-up table or database and correlated to the plaque content. In the preferred embodiment, each plaque or tissue component is assigned a range of signal properties representative of the component. The above-described process is summarized in FIG. 7.

The above-described process is repeated for each plaque or tissue component desired to be identified and repeated for each component as many times as desired in order to obtain a more accurate range of signal properties characteristic of the component. With the database built, given a set of signal properties taken from a backscatter signal, the signal properties can be automatically and accurately identified if the properties match a set of properties in the database.

Figure 8:
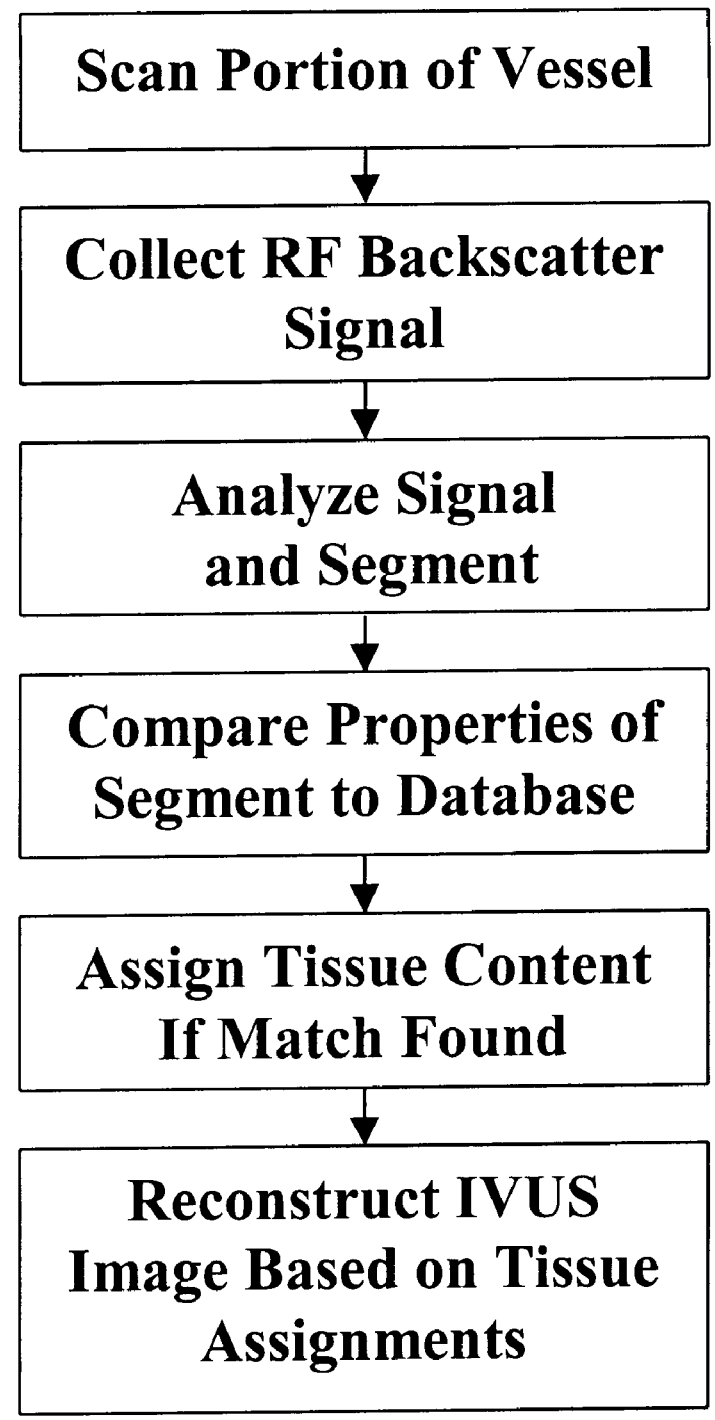
FIG. 8 illustrates a process for characterizing plaque in accordance with the present invention.
Figure 9:
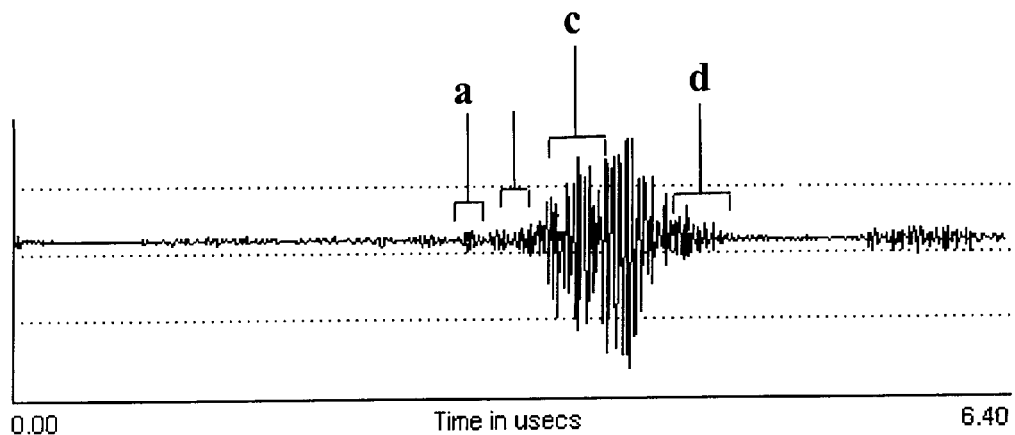
FIG. 9 illustrates a segmented scan line in accordance with the present invention.

Once the database is generated, plaque characterization of a blood vessel can be performed in vivo in an operating room in real-time with the following process which is summarized in FIG. 8. An ultrasonic transducer is carefully maneuvered through a patient's body within a blood vessel or other organ which is scanned and, ultrasonic backscatter signal data is collected. Frequency analysis is performed on each scan line of the raw backscatter signal to obtain signal properties for all portions of the backscatter signal. Each backscatter signal scan line is segmented based on its properties such that the properties within a segment are substantially similar. Thus, each segment represents a particular tissue or plaque content. FIG. 9 illustrates an exemplary segmentation of a scan line with segments a, b, c and d. Of course, a scan line may have any number of segments.

The signal properties from each signal segment a–d are then compared and matched to the signal properties in the database. If a match is found for a selected segment of the backscatter signal, the selected segment is correlated to the plaque component that corresponds to its signal properties of a segment. A match occurs as long as the signal properties fall within a range of properties for a plaque component found in the database. After the segments of the backscatter signal are identified, an IVUS image is reconstructed from the backscatter signal. Each area of the image constructed from a signal segment identified as a plaque component is distinguished from the other plaque components and tissues, for example with a different color. Thus, the contents of a vascular object are automatically identified in real-time while the patient is still on an operating table.

Figure 10A:
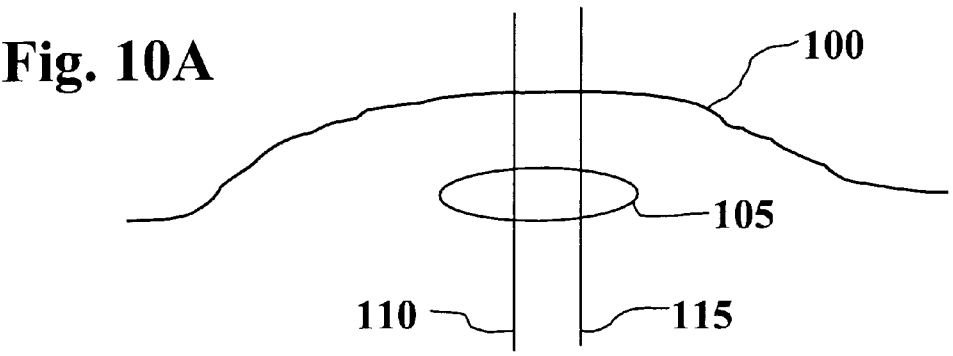
FIGS. 10A and 10B show a cross-section of a vessel wall and a lipid pool.
Figure 10B:
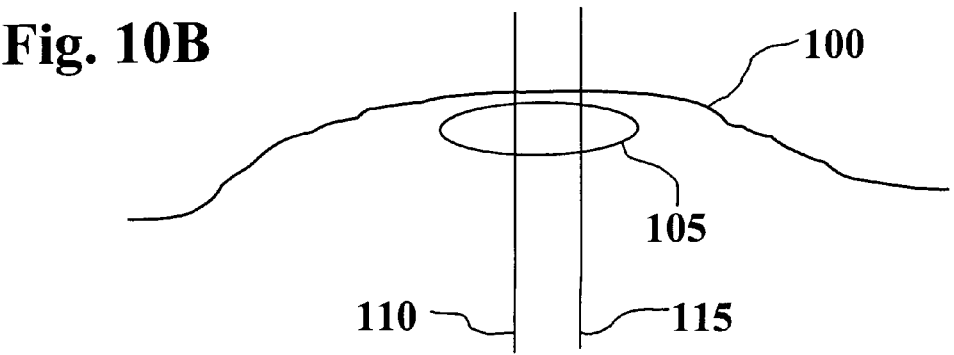

Since the backscatter signal has a property of time duration, the size and location of a plaque component can also be determined from the backscatter signal. An application of this is shown in FIGS. 10A and 10B. FIG. 10A illustrates an inner vessel wall 100 which includes a lipid pool 105 located within the vessel wall. This may be evaluated as a stable plaque due to the distance of the lipid pool 105 from the inner vessel wall. Conversely, FIG. 10B illustrates the lipid pool 105 located near the inner vessel wall 100 which is a potentially dangerous plaque. By analyzing the backscatter scan lines 110, 115 according to the present invention, the lipid pool can be identified, and also its relationship to other tissues within the vessel can be determined such as its distance from the inner vessel wall.

With reference again to FIG. 9, the relationship is determined by identifying the signal signature of the inner vessel wall 100 in the scan line by matching with the signal database. Then, its distance is determined along the scan lines to the lipid signal signature. For example, in the scan line shown, if a segment signature c represents the lipid pool 105 and the segment signature b represents the inner wall 100, this relationship represents a situation shown in FIG. 10B where the two components are near each other. Additionally, the area of the plaque can be determined by calculating the size of the plaque signal signature along each scan line and calculating its area. If three-dimensional data is acquired, then its volume can be calculated.

The invention has been described with reference to the preferred embodiment. Obviously, modifications and alterations will occur to others upon a reading and understanding of this specification. It is intended to include all such modifications and alterations insofar as they come within the scope of the appended claims or the equivalence thereof.

We claim:

1. A method of identifying components within a vascular object from an ultrasonic signal, the method comprising the steps of:

transmitting an ultrasonic signal within a selected region of the vascular object and collecting a backscatter signal reflected from the vascular object;

reconstructing an IVUS image of the selected region from the backscatter signal;

preparing a histology image of the selected region of the vascular object, the histology image distinguishing different components of the vascular object;

selecting a region of interest from the histology image, the region of interest representing one component from the different components of the vascular object and being at a coordinate location on the histology image;

mapping the coordinate location to a location on the IVUS image corresponding to the coordinate location;

translating the location on the IVUS image to a signal portion in the backscatter signal corresponding to the location, the signal portion representing a signal signature of the one component of the vascular object; and correlating the signal signature to the one component.

2. The method of identifying components as set forth in claim 1 further including performing a signal analysis on the signal portion to determine signal properties of the signal portion, the signal signature including the signal properties.

3. The method of identifying components as set forth in claim 2 further including storing the correlated signal signature and the one component in a database.

4. The method of identifying components as set forth in claim 1 further including:

selecting another region of interest from the histology image, the another region of interest representing another component from the different components of the vascular object;

repeating the mapping, translating and correlating steps to determine another signal signature which corresponds to the another component; and generating a database including the correlated signal signatures and the components.

5. The method of identifying components as set forth in claim 1 wherein the different components of the vascular object include plaque components.

6. The method of identifying components as set forth in claim 1 wherein the preparing includes digitizing the histology image.

7. A method of identifying components of a vascular object from an ultrasonic signal, the method comprising the steps of:

transmitting an ultrasonic signal within the vascular object, the vascular object reflecting portions of the ultrasonic signal and absorbing portions of the ultrasonic signal;

collecting the reflected portions of the ultrasonic signal as a backscatter signal, the backscatter signal including signal properties;

providing a database which associates vascular components to signal properties the database being pregenerated by correlating the vascular components from a histology image to corresponding signal properties from a backscatter signal;

comparing the signal properties of the backscatter signal to the signal properties in the database to determine a match; and assigning a vascular component to the signal properties of the backscatter signal if a match is determined.

8. The method of identifying components of a vascular object as set forth in claim 7 further including generating an intravascular ultrasound image from the backscatter signal, the ultrasound image distinguishing different vascular components based on the vascular component assigned to the signal properties of the backscatter signal.

9. The method of identifying components of a vascular object as set forth in claim 7 further including analyzing the backscatter signal to determine the signal properties, the signal properties including at least a frequency of the backscatter signal at a plurality of segments along the backscatter signal, each segment of the plurality of segments representing signal properties of a vascular component.

10. The method of identifying components of a vascular object as set forth in claim 9 further including determining a size of the vascular component based on a size of a segment in the backscatter signal that represents the vascular component.

11. The method of identifying components of a vascular object as set forth in claim 7 wherein the transmitting includes transmitting the ultrasonic signal in a plurality of scan lines, each of the scan lines including a backscatter signal reflected from the ultrasonic signal.

12. The method of identifying components of a vascular object as set forth in claim 11 further including analyzing the backscatter signal of each scan line to determine the signal properties at each of the plurality of segments.

13. The method of identifying components of a vascular object as set forth in 7 wherein the vascular component includes plaque.

14. The method of identifying components of a vascular object as set forth in 7 wherein the database correlates a range of signal properties to a vascular component.

15. The method of identifying components of a vascular object as set forth in 7 further including determining a relationship between two vascular components within the backscatter signal based on a location of the two vascular components along the backscatter signal.

16. A method for characterizing a plaque component within a vascular object based on an ultrasonic backscatter signal collected from a selected section of the vascular object, the method comprising the steps of:

preparing a histology image of the selected section of the vascular object;

selecting an area in the histology image which represents a plaque component;

corresponding the area in the histology image to a segment of the backscatter signal, the segment including signal properties; and associating the plaque component to the signal properties of the segment.

17. The method for characterizing a plaque component as set forth in claim 16 wherein the corresponding includes:

generating an ultrasonic image from the backscatter signal, the ultrasonic image having coordinates that correspond to coordinates of the histology image;

mapping the area in the histology image to a corresponding area in the ultrasonic image; and determining the segment of the backscatter signal that represents the corresponding area in the ultrasonic image.

18. The method for characterizing a plaque component as set forth in claim 16 further including performing a frequency analysis on the backscatter signal to determine the signal properties of the segment, the signal properties including at least a frequency of the segment.

19. The method for characterizing a plaque component as set forth in claim 18 further including performing a power spectrum analysis on the backscatter signal to determine power properties of the segment.

* * * * *